(12) United States Patent
Workman

(10) Patent No.: US 8,916,373 B2
(45) Date of Patent: Dec. 23, 2014

(54) MUTANT HUMAN SUPEROXIDE DISMUTASE 1 VARIANTS

(76) Inventor: Aron S Workman, Gainesville, FL (US)

( * ) Notice: Subject to any disclaimer, the term of this patent is extended or adjusted under 35 U.S.C. 154(b) by 289 days.

(21) Appl. No.: 13/150,676

(22) Filed: Jun. 1, 2011

(65) Prior Publication Data

US 2011/0294190 A1 Dec. 1, 2011

Related U.S. Application Data

(60) Provisional application No. 61/350,020, filed on Jun. 1, 2010.

(51) Int. Cl.
*C12N 1/20* (2006.01)
*C12N 9/02* (2006.01)
*C07H 21/04* (2006.01)

(52) U.S. Cl.
CPC ....... *C12N 9/0089* (2013.01); *C12Y 115/01001* (2013.01)

USPC ...................................... 435/252.3; 536/23.2

(58) Field of Classification Search
USPC ............................... 435/189, 252.3; 536/23.2
See application file for complete search history.

(56) References Cited

PUBLICATIONS

Sequence alignment between AC P00443 and Applicants SEQ ID No. 1. (1986).*

* cited by examiner

*Primary Examiner* — Tekchand Saidha

(57) ABSTRACT

The present invention in the art of biochemistry claims novel and non-naturally occurring mutant human superoxide dismutase 1 (hsod1) variant polypeptides, their encoding nucleic acids, and recombinant cells thereof. The inventor rationally designed mutant hsod1 variants using structural observations and complimentary experimentation. The designed mutant hsod1 variant products claimed have multiple potential industrial applications including as novel therapeutics.

5 Claims, 3 Drawing Sheets

SEQUENCE LISTING

<160> NUMBER OF SEQ ID NOS: 17

<210> SEQ ID NO 1
<211> LENGTH: 153
<212> TYPE: PRT
<213> ORGANISM: Homo sapiens

<400> SEQUENCE: 1

```
Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60
```

```
Asn Pro Leu Ser Arg Lys His Gly Gly Pro Lys Asp Glu Arg His
65                  70                  75                  80

Val Gly Asp Leu Gly Asn Val Thr Ala Asp Lys Asp Gly Val Ala Asp
                85                  90                  95

Val Ser Ile Glu Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150

<210> SEQ ID NO 2
<211> LENGTH: 153
<212> TYPE: PRT
<213> ORGANISM: Artificial Sequence
<220> FEATURE:
<221> NAME/KEY: Glu21Gln
<223> OTHER INFORMATION: Novel mutant human superoxide dismutase 1
      variant

<400> SEQUENCE: 2

Ala Thr Lys Ala Val Cys Val Leu Lys Gly Asp Gly Pro Val Gln Gly
1               5                   10                  15

Ile Ile Asn Phe Gln Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Glu Arg His
65                  70                  75                  80

Val Gly Asp Leu Gly Asn Val Thr Ala Asp Lys Asp Gly Val Ala Asp
                85                  90                  95

Val Ser Ile Glu Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150

<210> SEQ ID NO 3
<211> LENGTH: 153
<212> TYPE: PRT
<213> ORGANISM: Artificial Sequence
<220> FEATURE:
<221> NAME/KEY: Glu21Asn
<223> OTHER INFORMATION: Novel mutant human superoxide dismutase 1
      variant

<400> SEQUENCE: 3

Ala Thr Lys Ala Val Cys Val Leu Lys Gly Asp Gly Pro Val Gln Gly
1               5                   10                  15

Ile Ile Asn Phe Asn Gln Lys Glu Ser Asn Gly Pro Val Lys Val Trp
            20                  25                  30
```

```
Gly Ser Ile Lys Gly Leu Thr Glu Gly Leu His Gly Phe His Val His
            35                  40                  45

Glu Phe Gly Asp Asn Thr Ala Gly Cys Thr Ser Ala Gly Pro His Phe
 50                  55                  60

Asn Pro Leu Ser Arg Lys His Gly Gly Pro Lys Asp Glu Glu Arg His
 65                  70                  75                  80

Val Gly Asp Leu Gly Asn Val Thr Ala Asp Lys Asp Gly Val Ala Asp
                 85                  90                  95

Val Ser Ile Glu Asp Ser Val Ile Ser Leu Ser Gly Asp His Cys Ile
                100                 105                 110

Ile Gly Arg Thr Leu Val Val His Glu Lys Ala Asp Asp Leu Gly Lys
                115                 120                 125

Gly Gly Asn Glu Glu Ser Thr Lys Thr Gly Asn Ala Gly Ser Arg Leu
            130                 135                 140

Ala Cys Gly Val Ile Gly Ile Ala Gln
145                 150
```

<210> SEQ ID NO 4
<211> LENGTH: 153
<212> TYPE: PRT
<213> ORGANISM: Artificial Sequence
<220> FEATURE:
<221> NAME/KEY: Glu24Gln
<223> OTHER INFORMATION: Novel mutant human superoxide dismutase 1 variant

<400> SEQUENCE: 4

```
Ala Thr Lys Ala Val Cys Val Leu Lys Gly Asp Gly Pro Val Gln Gly
 1               5                  10                  15

Ile Ile Asn Phe Glu Gln Lys Gln Ser Asn Gly Pro Val Lys Val Trp
                20                  25                  30

Gly Ser Ile Lys Gly Leu Thr Glu Gly Leu His Gly Phe His Val His
            35                  40                  45

Glu Phe Gly Asp Asn Thr Ala Gly Cys Thr Ser Ala Gly Pro His Phe
 50                  55                  60

Asn Pro Leu Ser Arg Lys His Gly Gly Pro Lys Asp Glu Glu Arg His
 65                  70                  75                  80

Val Gly Asp Leu Gly Asn Val Thr Ala Asp Lys Asp Gly Val Ala Asp
                 85                  90                  95

Val Ser Ile Glu Asp Ser Val Ile Ser Leu Ser Gly Asp His Cys Ile
                100                 105                 110

Ile Gly Arg Thr Leu Val Val His Glu Lys Ala Asp Asp Leu Gly Lys
                115                 120                 125

Gly Gly Asn Glu Glu Ser Thr Lys Thr Gly Asn Ala Gly Ser Arg Leu
            130                 135                 140

Ala Cys Gly Val Ile Gly Ile Ala Gln
145                 150
```

<210> SEQ ID NO 5
<211> LENGTH: 153
<212> TYPE: PRT
<213> ORGANISM: Artificial Sequence
<220> FEATURE:
<221> NAME/KEY: Glu24Asn
<223> OTHER INFORMATION: Novel mutant human superoxide dismutase 1 variant

<400> SEQUENCE: 5

Ala Thr Lys Ala Val Cys Val Leu Lys Gly Asp Gly Pro Val Gln Gly

```
                1               5                      10                      15
Ile Ile Asn Phe Glu Gln Lys Asn Ser Asn Gly Pro Val Lys Val Trp
                        20                      25                      30

Gly Ser Ile Lys Gly Leu Thr Glu Gly Leu His Gly Phe His Val His
                        35                      40                      45

Glu Phe Gly Asp Asn Thr Ala Gly Cys Thr Ser Ala Gly Pro His Phe
            50                      55                      60

Asn Pro Leu Ser Arg Lys His Gly Gly Pro Lys Asp Glu Glu Arg His
65                      70                      75                      80

Val Gly Asp Leu Gly Asn Val Thr Ala Asp Lys Asp Gly Val Ala Asp
                        85                      90                      95

Val Ser Ile Glu Asp Ser Val Ile Ser Leu Ser Gly Asp His Cys Ile
                        100                     105                     110

Ile Gly Arg Thr Leu Val Val His Glu Lys Ala Asp Asp Leu Gly Lys
                        115                     120                     125

Gly Gly Asn Glu Glu Ser Thr Lys Thr Gly Asn Ala Gly Ser Arg Leu
            130                     135                     140

Ala Cys Gly Val Ile Gly Ile Ala Gln
145                     150

<210> SEQ ID NO 6
<211> LENGTH: 153
<212> TYPE: PRT
<213> ORGANISM: Artificial Sequence
<220> FEATURE:
<221> NAME/KEY: Glu40Gln
<223> OTHER INFORMATION: Novel mutant human superoxide dismutase 1
      variant

<400> SEQUENCE: 6

Ala Thr Lys Ala Val Cys Val Leu Lys Gly Asp Gly Pro Val Gln Gly
1               5                       10                      15

Ile Ile Asn Phe Glu Gln Lys Glu Ser Asn Gly Pro Val Lys Val Trp
                        20                      25                      30

Gly Ser Ile Lys Gly Leu Thr Gln Gly Leu His Gly Phe His Val His
                        35                      40                      45

Glu Phe Gly Asp Asn Thr Ala Gly Cys Thr Ser Ala Gly Pro His Phe
            50                      55                      60

Asn Pro Leu Ser Arg Lys His Gly Gly Pro Lys Asp Glu Glu Arg His
65                      70                      75                      80

Val Gly Asp Leu Gly Asn Val Thr Ala Asp Lys Asp Gly Val Ala Asp
                        85                      90                      95

Val Ser Ile Glu Asp Ser Val Ile Ser Leu Ser Gly Asp His Cys Ile
                        100                     105                     110

Ile Gly Arg Thr Leu Val Val His Glu Lys Ala Asp Asp Leu Gly Lys
                        115                     120                     125

Gly Gly Asn Glu Glu Ser Thr Lys Thr Gly Asn Ala Gly Ser Arg Leu
            130                     135                     140

Ala Cys Gly Val Ile Gly Ile Ala Gln
145                     150

<210> SEQ ID NO 7
<211> LENGTH: 153
<212> TYPE: PRT
<213> ORGANISM: Artificial Sequence
<220> FEATURE:
<221> NAME/KEY: Glu40Asn
<223> OTHER INFORMATION: Novel mutant human superoxide dismutase 1
```

-continued variant

<400> SEQUENCE: 7

Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Asn Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Glu Glu Arg His
65                  70                  75                  80

Val Gly Asp Leu Gly Asn Val Thr Ala Asp Lys Asp Gly Val Ala Asp
                85                  90                  95

Val Ser Ile Glu Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150

<210> SEQ ID NO 8
<211> LENGTH: 153
<212> TYPE: PRT
<213> ORGANISM: Artificial Sequence
<220> FEATURE:
<221> NAME/KEY: Glu77Gln
<223> OTHER INFORMATION: Novel mutant human superoxide dismutase 1 variant

<400> SEQUENCE: 8

Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Gln Glu Arg His
65                  70                  75                  80

Val Gly Asp Leu Gly Asn Val Thr Ala Asp Lys Asp Gly Val Ala Asp
                85                  90                  95

Val Ser Ile Glu Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150

<210> SEQ ID NO 9
<211> LENGTH: 153

```
<212> TYPE: PRT
<213> ORGANISM: Artificial Sequence
<220> FEATURE:
<221> NAME/KEY: Glu77Asn
<223> OTHER INFORMATION: Novel mutant human superoxide dismutase 1
      variant

<400> SEQUENCE: 9

Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Asn Glu Arg His
65                  70                  75                  80

Val Gly Asp Leu Gly Asn Val Thr Ala Asp Lys Asp Gly Val Ala Asp
                85                  90                  95

Val Ser Ile Glu Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150

<210> SEQ ID NO 10
<211> LENGTH: 153
<212> TYPE: PRT
<213> ORGANISM: Artificial Sequence
<220> FEATURE:
<221> NAME/KEY: Glu78Gln
<223> OTHER INFORMATION: Novel mutant human superoxide dismutase 1
      variant

<400> SEQUENCE: 10

Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Glu Gln Arg His
65                  70                  75                  80

Val Gly Asp Leu Gly Asn Val Thr Ala Asp Lys Asp Gly Val Ala Asp
                85                  90                  95

Val Ser Ile Glu Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
```

<210> SEQ ID NO 11
<211> LENGTH: 153
<212> TYPE: PRT
<213> ORGANISM: Artificial Sequence
<220> FEATURE:
<221> NAME/KEY: Glu78Asn
<223> OTHER INFORMATION: Novel mutant human superoxide dismutase 1 variant

<400> SEQUENCE: 11

```
Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Glu Asn Arg His
65                  70                  75                  80

Val Gly Asp Leu Gly Asn Val Thr Ala Asp Lys Asp Gly Val Ala Asp
                85                  90                  95

Val Ser Ile Glu Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150
```

<210> SEQ ID NO 12
<211> LENGTH: 153
<212> TYPE: PRT
<213> ORGANISM: Artificial Sequence
<220> FEATURE:
<221> NAME/KEY: Glu100Gln
<223> OTHER INFORMATION: Novel mutant human superoxide dismutase 1 variant

<400> SEQUENCE: 12

```
Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Glu Glu Arg His
65                  70                  75                  80

Val Gly Asp Leu Gly Asn Val Thr Ala Asp Lys Asp Gly Val Ala Asp
                85                  90                  95

Val Ser Ile Gln Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125
```

```
Gly Gly Asn Glu Glu Ser Thr Lys Thr Gly Asn Ala Gly Ser Arg Leu
        130                 135                 140

Ala Cys Gly Val Ile Gly Ile Ala Gln
145                 150

<210> SEQ ID NO 13
<211> LENGTH: 153
<212> TYPE: PRT
<213> ORGANISM: Artificial Sequence
<220> FEATURE:
<221> NAME/KEY: Glu100Asn
<223> OTHER INFORMATION: Novel mutant human superoxide dismutase 1
      variant

<400> SEQUENCE: 13

Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Glu Glu Arg His
65                  70                  75                  80

Val Gly Asp Leu Gly Asn Val Thr Ala Asp Lys Asp Gly Val Ala Asp
                85                  90                  95

Val Ser Ile Asn Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150

<210> SEQ ID NO 14
<211> LENGTH: 153
<212> TYPE: PRT
<213> ORGANISM: Artificial Sequence
<220> FEATURE:
<221> NAME/KEY: Glu121Gln
<223> OTHER INFORMATION: Novel mutant human superoxide dismutase 1
      variant

<400> SEQUENCE: 14

Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Glu Glu Arg His
65                  70                  75                  80

Val Gly Asp Leu Gly Asn Val Thr Ala Asp Lys Asp Gly Val Ala Asp
                85                  90                  95
```

```
Val Ser Ile Glu Asp Ser Val Ile Ser Leu Ser Gly Asp His Cys Ile
            100                 105                 110

Ile Gly Arg Thr Leu Val Val His Gln Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150

<210> SEQ ID NO 15
<211> LENGTH: 153
<212> TYPE: PRT
<213> ORGANISM: Artificial Sequence
<220> FEATURE:
<221> NAME/KEY: Glu121Asn
<223> OTHER INFORMATION: Novel mutant human superoxide dismutase 1
      variant

<400> SEQUENCE: 15

Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Glu Glu Arg His
65                  70                  75                  80

Val Gly Asp Leu Gly Asn Val Thr Ala Asp Lys Asp Gly Val Ala Asp
                85                  90                  95

Val Ser Ile Glu Asp Ser Val Ile Ser Leu Ser Gly Asp His Cys Ile
            100                 105                 110

Ile Gly Arg Thr Leu Val Val His Asn Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150

<210> SEQ ID NO 16
<211> LENGTH: 153
<212> TYPE: PRT
<213> ORGANISM: Artificial Sequence
<220> FEATURE:
<221> NAME/KEY: Glu132Asn
<223> OTHER INFORMATION: Novel mutant human superoxide dismutase 1
      variant

<400> SEQUENCE: 16

Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Glu Glu Arg His
```

```
                       65                    70                    75                    80
Val Gly Asp Leu Gly Asn Val Thr Ala Asp Lys Asp Gly Val Ala Asp
                    85                    90                    95

Val Ser Ile Glu Asp Ser Val Ile Ser Leu Ser Gly Asp His Cys Ile
                   100                   105                   110

Ile Gly Arg Thr Leu Val Val His Glu Lys Ala Asp Asp Leu Gly Lys
                115                   120                   125

Gly Gly Asn Asn Glu Ser Thr Lys Thr Gly Asn Ala Gly Ser Arg Leu
            130                   135                   140

Ala Cys Gly Val Ile Gly Ile Ala Gln
145                 150

<210> SEQ ID NO 17
<211> LENGTH: 153
<212> TYPE: PRT
<213> ORGANISM: Artificial Sequence
<220> FEATURE:
<221> NAME/KEY: Glu133Asn
<223> OTHER INFORMATION: Novel mutant human superoxide dismutase 1
      variant

<400> SEQUENCE: 17

Ala Thr Lys Ala Val Cys Val Leu Lys Gly Asp Gly Pro Val Gln Gly
1               5                  10                   15

Ile Ile Asn Phe Glu Gln Lys Glu Ser Asn Gly Pro Val Lys Val Trp
               20                   25                   30

Gly Ser Ile Lys Gly Leu Thr Glu Gly Leu His Gly Phe His Val His
            35                   40                   45

Glu Phe Gly Asp Asn Thr Ala Gly Cys Thr Ser Ala Gly Pro His Phe
    50                   55                   60

Asn Pro Leu Ser Arg Lys His Gly Gly Pro Lys Asp Glu Glu Arg His
65                   70                   75                   80

Val Gly Asp Leu Gly Asn Val Thr Ala Asp Lys Asp Gly Val Ala Asp
                    85                    90                    95

Val Ser Ile Glu Asp Ser Val Ile Ser Leu Ser Gly Asp His Cys Ile
                   100                   105                   110

Ile Gly Arg Thr Leu Val Val His Glu Lys Ala Asp Asp Leu Gly Lys
                115                   120                   125

Gly Gly Asn Glu Asn Ser Thr Lys Thr Gly Asn Ala Gly Ser Arg Leu
            130                   135                   140

Ala Cys Gly Val Ile Gly Ile Ala Gln
145                 150
```

MUTANT HUMAN SUPEROXIDE DISMUTASE 1 VARIANTS

CROSS-REFERENCE TO RELATED APPLICATIONS

This invention claims priority from provisional application No. 61/350,020, filed 1 Jun., 2010.

STATEMENT REGARDING FEDERALLY SPONSORED RESEARCH

To reduce the invention to practice, the inventor incurred costs to the National Institutes of Health Grant No. NS-049134 at the University of Florida (Gainesville, Fla., U.S.).

REFERENCE TO POLYPEPTIDE SEQUENCE LISTINGS

SEQ ID NO: 1—wild-type human superoxide dismutase 1 (hsod1)
SEQ ID NO: 2—novel mutant hsod1 variant Glu21Gln
SEQ ID NO: 3—novel mutant hsod1 variant Glu21Asn
SEQ ID NO: 4—novel mutant hsod1 variant Glu24Gln
SEQ ID NO: 5—novel mutant hsod1 variant Glu24Asn
SEQ ID NO: 6—novel mutant hsod1 variant Glu40 Gln
SEQ ID NO: 7—novel mutant hsod1 variant Glu40Asn
SEQ ID NO: 8—novel mutant hsod1 variant Glu77Gln
SEQ ID NO: 9—novel mutant hsod1 variant Glu77Asn
SEQ ID NO: 10—novel mutant hsod1 variant Glu78Gln
SEQ ID NO: 11—novel mutant hsod1 variant Glu78Asn
SEQ ID NO: 12—novel mutant hsod1 variant Glu100Gln
SEQ ID NO: 13—novel mutant hsod1 variant Glu100Asn
SEQ ID NO: 14—novel mutant hsod1 variant Glu121Gln
SEQ ID NO: 15—novel mutant hsod1 variant Glu121Asn
SEQ ID NO: 16—novel mutant hsod1 variant Glu132Asn
SEQ ID NO: 17—novel mutant hsod1 variant Glu133Asn

BACKGROUND OF THE INVENTION

1. Field of the Invention

This invention in the art of biochemistry relates to novel and non-naturally occurring mutant human superoxide dismutase 1 (hsod1) variant polypeptides, their encoding nucleic acids, and recombinant cells containing those nucleic acids. The mutant hsod1 products claimed have many potential industrial applications including as novel therapeutics.

2. Description of the Related Art

A mutant hsod1 variant is a polypeptide having one or more substituted residues distinct from that of wild-type hsod1. Hundreds of naturally occurring mutant hsod1 variants have been reported and several non-naturally occurring mutant hsod1 variants have been engineered thus far (Getzoff E D, et al (1992) Faster superoxide dismutase mutants designed by enhancing electrostatic guidance. *Nature* 358: 347-351). The mutant hsod1 variants claimed in the present invention are both entirely novel and non-naturally occurring.

BRIEF SUMMARY OF THE INVENTION

The present invention claims novel and non-naturally occurring mutant human superoxide dismutase 1 (hsod1) variant polypeptides, their encoding nucleic acids, and recombinant cells thereof.

Employing structural observations and complimentary experimentation, the inventor rationally engineered non-naturally occurring mutant hsod1 variants.

The engineered mutant hsod1 variant products claimed have multiple potential industrial applications, including as novel therapeutics.

The inventor synthesized recombinant nucleic acids encoding the claimed mutant hsod1 variants and expressed those recombinant nucleic acids in host cell cultures to produce and analyze the resultant novel mutant hsod1 polypeptides.

The novel mutant hsod1 variants claimed in the present invention are, relative to wild-type hsod1 (SEQ ID NO: 1):
Glu21Gln (SEQ ID NO: 2) and Glu21Asn (SEQ ID NO: 3);
Glu24Gln (SEQ ID NO: 4) and Glu24Asn (SEQ ID NO: 5);
Glu40Gln (SEQ ID NO: 6) and Glu40Asn (SEQ ID NO: 7);
Glu77Gln (SEQ ID NO: 8) and Glu77Asn (SEQ ID NO: 9);
Glu78Gln (SEQ ID NO: 10) and Glu78Asn (SEQ ID NO: 11);
Glu100Gln (SEQ ID NO: 12) and Glu100Asn (SEQ ID NO: 13);
Glu121Gln (SEQ ID NO: 14) and Glu121Asn (SEQ ID NO: 15);
Glu132Asn (SEQ ID NO: 16); and
Glu133Asn (SEQ ID NO: 17).

BRIEF DESCRIPTION OF THE SEVERAL VIEWS OF THE DRAWINGS

Both

The crystal structure analyzed is fully metallated wild-type homodimer at 1.07 angstrom resolution (Strange R W, et al (2006) Variable metallation of human superoxide dismutase: Atomic resolution crystal structures of cu-zn, zn-zn and as-isolated wild-type enzymes. *J Mol Biol* 356: 1152-1162), ID 2c9v stored in the Protein Data Bank (Berman H M, et al (2000) The protein data bank. *Nucleic Acids Research* 28: 235-242). The program PyMOL was used for molecular imaging (DeLano W L (2002) The PyMOL molecular graphics system).

Figure 1A:
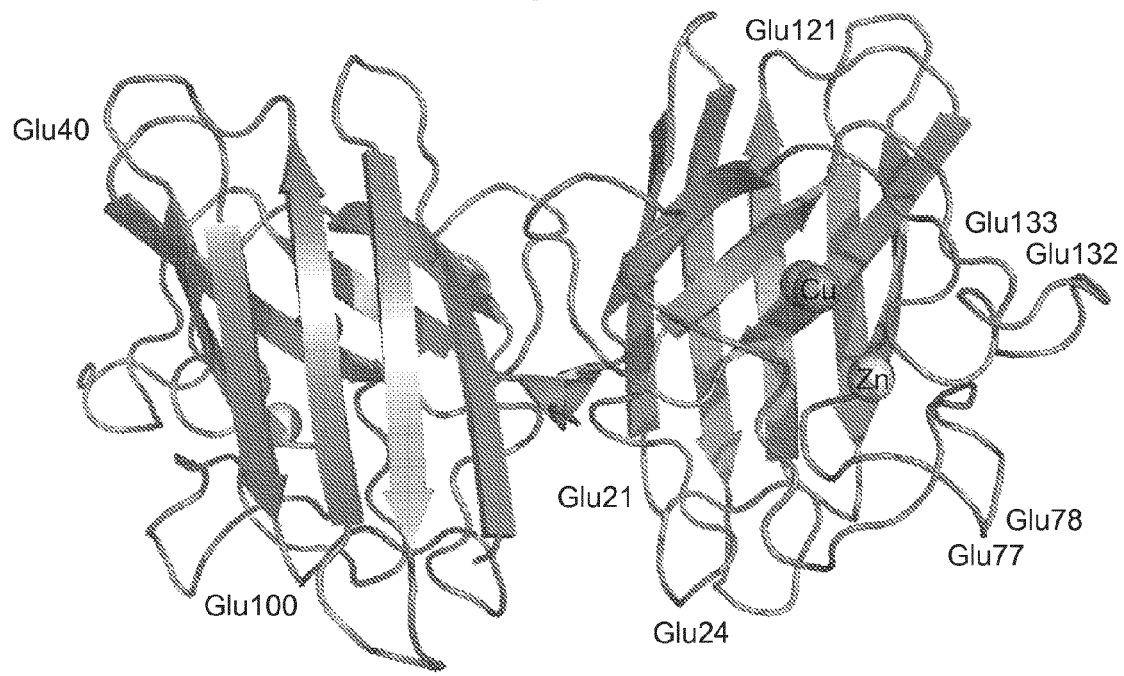
FIGS. 1 and 2 are diagrams used to illustrate and disclose the superoxide motifs discovered in the distal loops of "human superoxide dismutase 1" (hsod1). The discovery of the superoxide motifs enabled the mutant hsod1 variants claimed in the present invention.
Figure 1B:
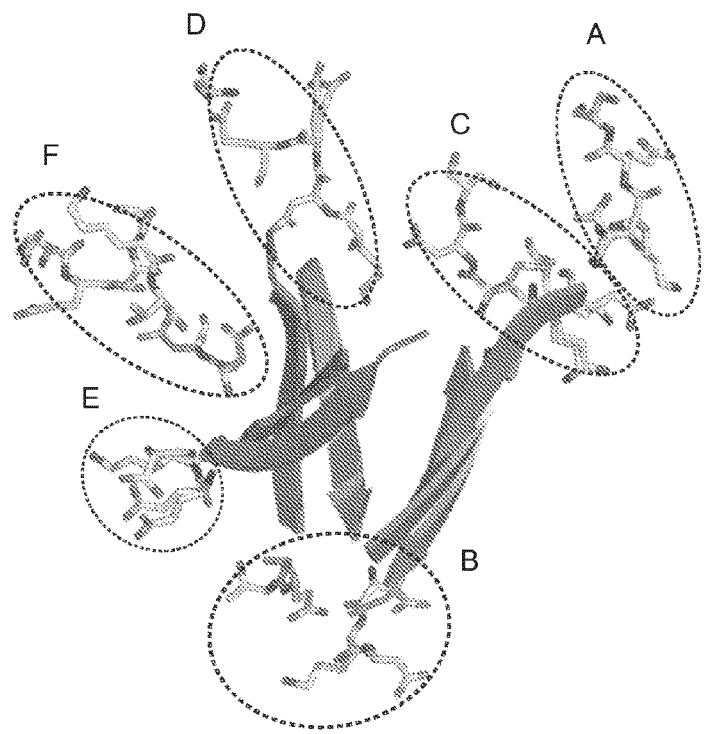

FIGS. 1A-B are ribbon/stick whole dimer and monomer cutaway diagrams presenting the structure of hsod1 with identification of the novel superoxide motifs and their enzymatically critical Glu residues:

FIG. 1A is a total structure near-symmetrical dimer ribbon diagram including the generalized locations of the enzymatically critical Glu residues; and FIG. 1B is a side view of a monomer ribbon diagram wherein superoxide motifs are represented as sticks, and extraneous loop residues and metals are removed for clarity. Each superoxide ionophore motif is encompassed in dotted ellipses and its corresponding cut-away referenced by letter (corresponding to FIGS. 2A-F).

FIGS. 2A-F are crystal structure cutaway diagrams identified by residue displaying the six isolated superoxide motifs.

Figure 2A:
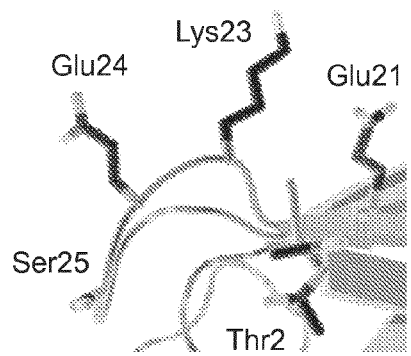
Figure 2B:
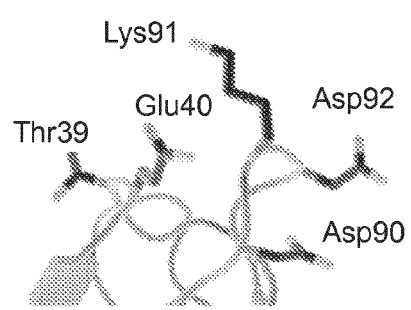
Figure 2C:
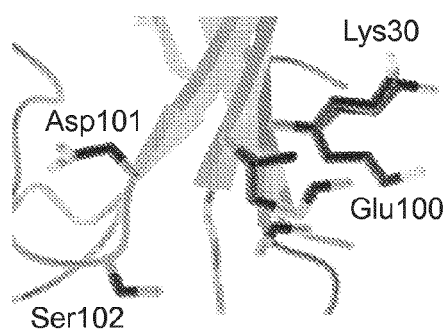
Figure 2D:
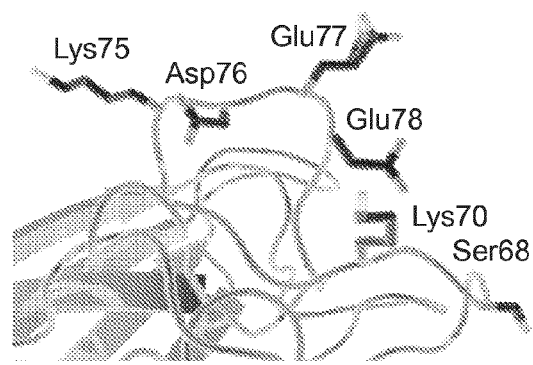
Figure 2E:
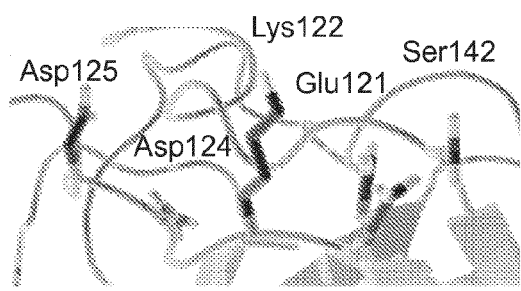

The following superoxide motifs are featured in the figures, where each residue within each motif is separated by a comma:

FIG. 2A and 'A' in FIG. 1B: Thr2, Glu21, Lys23, Glu24, Ser25;

FIG. 2B and 'B' in FIG. 1B: Ser68, Lys70, Lys75, Asp76, Glu77, Glu78;

FIG. 2C and 'C' in FIG. 1B: Thr39, Glu40, Asp90, Lys91, Asp92;

FIG. 2D and 'D' in FIG. 1B: Lys30, Glu100, Asp101, Ser102;

FIG. 2E and 'E' in FIG. 1B: Glu121, Lys122, Asp124, Asp125, Ser142; and

Figure 2F:
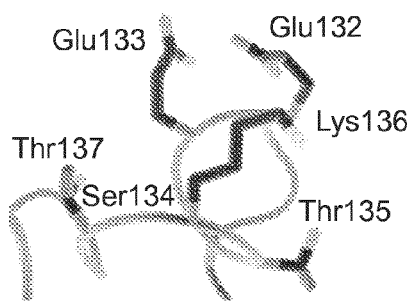

FIG. 2F and 'F' in FIG. 1B: Glu132, Glu133, Ser134, Thr135, Lys136, Thr137.

Figure 3:
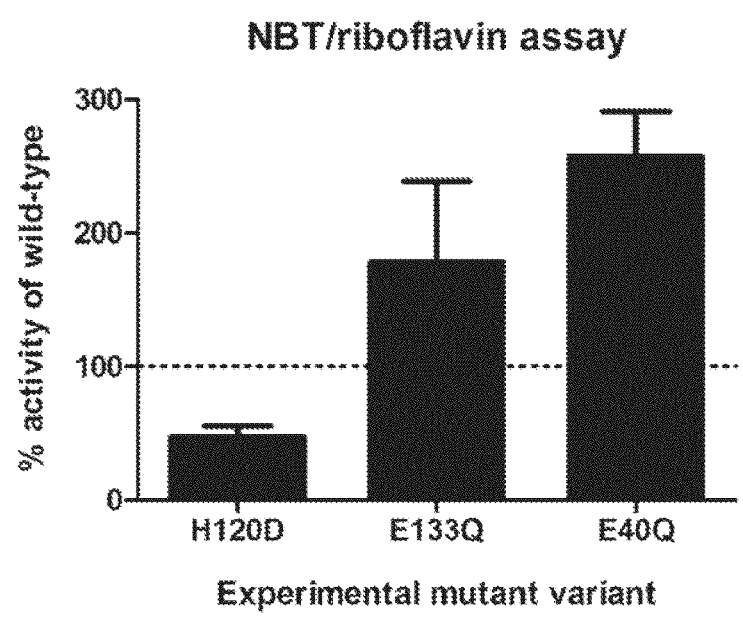

FIG. 3: Statistical proof given by riboflavin/nitroblue tetrazolium activity assay.

DETAILED DESCRIPTION OF THE INVENTION

The present invention claims novel mutant "human superoxide dismutase 1" (hsod1) variant polypeptides, their encoding nucleic acids, and recombinant cells thereof.

The non-naturally occurring mutant hsod1 variants claimed in the present invention are engineered for increased enzymatic activity, or hyperactivity, relative to wild-type hsod1. The activity of an enzyme is the rate at which that enzyme catalyzes its substrate to product.

Hyperactive mutant hsod1 variants are therefore ideal for industrial applications. In one potential embodiment of the present invention, compositions comprising claimed mutant hsod1 polypeptides may be directly utilized as novel recombinant therapeutics.

The present invention uses terms of the art including "nucleic acid", "wild-type", "recombinant", "transgenic", "variant", "residue", "mutant", and etcetera. These terms are widely used and understood in the fields of biochemistry and molecular biology (Setubal C & Meidanis J (1997) *Introduction to Computational Molecular Biology*, PWS Publishing, pp 320; Karp G (2007) *Cell and Molecular Biology: Concepts and Experiments*, Wiley, pp 864; Sambrook J (2001) *Molecular Cloning: A Laboratory Manual*, Cold Spring Harbor Laboratory Press, pp 999).

Wild-type superoxide dismutase 1 (superoxide:superoxide oxidoreductase, EC 1.15.1.1, human isoform SEQ ID NO: 1) is a copper/zinc-containing homodimeric enzyme found in the intracellular space of all aerobic organisms. Superoxide dismutase 1 catalyzes the reaction of toxic superoxide anion radical to hydrogen peroxide and water.

Human superoxide dismutase 1 is a historical object of study because:

It is a primary antioxidant implicated in myriad physiological processes including homeostasis, metabolism, inflammation, aging, and etcetera;

It is a historical therapeutic; and

Particular mutant variants initiate and sustain the paralytic neuromuscular disease hsod1-implicated familial Amyotrophic Lateral Sclerosis.

The inventor studied and screened multiple publically available crystal structures of superoxide dismutases, and from that work identified common structural motifs in their distal loops.

The identified structural motifs are likely arranged to first receive the superoxide anion substrate, as they are located on the exterior of the protein and mutating them affects global enzymatic activity considerably. Because of this apparent function, said structural motifs may be referred to as "superoxide ionophores".

The superoxide ionophores typically manifest in superoxide dismutase x-ray crystal structures as multiple carboxyl residues (Asp or Glu) and one or two alcohol residue(s) (Thr or Ser) geometrically coordinating a Lys residue by hydrogen bonding.

The following novel superoxide ionophores have been discovered on the exterior of hsod1, where each residue within each motif is separated by a comma:

FIG. 2A and 'A' in FIG. 1B: Thr2, Glu21, Lys23, Glu24, Ser25;

FIG. 2B and 'B' in FIG. 1B: Ser68, Lys70, Lys75, Asp76, Glu77, Glu78;

FIG. 2C and 'C' in FIG. 1B: Thr39, Glu40, Asp90, Lys91, Asp92;

FIG. 2D and D' in FIG. 1B: Lys30, Glu100, Asp101, Ser102;

FIG. 2E and 'E' in FIG. 1B: Glu121, Lys122, Asp124, Asp125, Ser142; and

FIG. 2F and 'F' in FIG. 1B: Glu132, Glu133, Ser134, Thr135, Lys136, Thr137.

That there are six superoxide ionophores on the exterior of hsod1 that modulate hsod1's global enzymatic activity is the novel and enabling observation that led to the engineering of the mutant hsod1 variants claimed in the present invention.

The inventor experimentally manipulated the discovered hsod1 superoxide ionophores, with emphasis on single-atom and single-atom delete branch mutants in effort to minimize disruption to the structure of the superoxide ionophore. Of a relatively extensive screening, substitutions of particular Glu residues in hsod1 were found to be the only significantly active mutant variants relative to wild-type, and of those, the Glu to Gln substitution variants proved most active and more active than wild-type on all accounts.

Significantly, objective assays have experimentally validated the hyperactivity of the novel mutant hsod1 variants claimed regardless of the current state or ultimate validity of the superoxide ionophore hypothesis.

The novel mutant hsod1 variants claimed in the present invention are, relative to wild-type hsod1 (SEQ ID NO: 1):

Glu21Gln (SEQ ID NO: 2) and Glu21Asn (SEQ ID NO: 3);

Glu24Gln (SEQ ID NO: 4) and Glu24Asn (SEQ ID NO: 5);

Glu40Gln (SEQ ID NO: 6) and Glu40Asn (SEQ ID NO: 7);

Glu77Gln (SEQ ID NO: 8) and Glu77Asn (SEQ ID NO: 9);

Glu78Gln (SEQ ID NO: 10) and Glu78Asn (SEQ ID NO: 11);

Glu100Gln (SEQ ID NO: 12) and Glu100Asn (SEQ ID NO: 13);

Glu121Gln (SEQ ID NO: 14) and Glu121Asn (SEQ ID NO: 15);

Glu132Asn (SEQ ID NO: 16); and

Glu133Asn (SEQ ID NO: 17).

Each mutant variant claimed may be used individually for anywhere from approximately 1.5 to over three times increased enzymatic activity relative to wild-type. Glu40Gln is the most hyperactive single mutant variant.

The most hyperactive mutant hsod1 variants are compound mutant variants: those variants that contain multiple mutant substitutions within the same molecule.

The double compound mutant variant Glu40Gln/Glu133Gln is very active and has several times the enzymatic activity of wild-type, as do the triple compound mutant variants Glu21Gln/Glu40Gln/Glu77Gln and Glu40Gln/Glu100Gln/Glu121Gln, and the quadruple compound mutant variant Glu21Gln/Glu40Gln/Glu77Gln/Glu133Gln.

The inventor discovered that while altering a single superoxide ionophore at multiple residues within one molecule (for examples Glu21Gln/Glu24Gln or Glu132Gln/Glu133Gln) shows only a modest increase in activity relative to one or the other single mutant alone, compound mutant hsod1 variants containing mutations across multiple ionophores (for examples Glu40Gln/Glu133Gln, Glu21Gln/Glu40Gln/Glu77Gln, and etcetera) have seemingly additive global enzymatic activity.

At the present time it is trusted that the six compound mutant hsod1 variant Glu21Gln/Glu40Gln/Glu77Gln/Glu100Gln/Glu121Gln/Glu133Gln has the greatest enzymatic activity of any hsod1 or any other superoxide dismutase yet reported in the literature. The six compound mutant hsod1 variant is presently the best known mode of the invention.

Without further elaboration, it is believed that one skilled in the art can, using the disclosed identities of the claimed mutations alone, utilize the present invention to its fullest extent. The following specific embodiments are therefore merely illustrative, and not limitative of the remainder of the disclosure or claims in any way whatsoever:

Example 1

Construction and Characterization of Purified Nucleic Acids Encoding Mutant Superoxide Dismutase 1 Genes Superoxide dismutase 1 nucleic acid encoded in the mammalian expression vector plasmid pEF-BOS from dictionary were prepared by double CsCl/EtBr density gradient and confirmed by automated sequencing and agarose electrophoresis (Mizushima S & Nagata S (1990) pEF-BOS, a powerful mammalian expression vector. *Nucl Acids Res* 18: 5322). Point mutants were introduced by standard PCR-directed mutagenesis with a high-proof polymerase and two unique primers per mutant. Compound mutants were created step-wise by point mutating each successively purified recombinant nucleic acid.

Example 2

Production of Mutant Hsod1 Variant Polypeptides

Four micrograms recombinant nucleic acid transfectant was prepared with Lipofectamine 2000 (Invitrogen, Inc.) and added to confluent 60 mm dishes of human embryonic kidney cells (HEK cells, line HEK293FT) or mouse embryonic fibroblasts (3T3s, line NIH 3T3). Media was added four hours later. HEK cell expression began six hours post-transfection and stabilized between 12 and 18 hours post-transfection at high levels of intracellular expression. Cell pellets were harvested in phosphate buffered saline (PBS) using a sonicator.

Example 3

Detection of Mutant Hsod1 Variant Polypeptides

To detect mutant polypeptide expression a standard immunoblot was performed. Polypeptide concentrations were determined by a bicinchoninic acid assay (with bovine serum albumin standard) and equivalent amounts of polypeptide were boiled at 96° Celsius for six minutes and loaded on 18% tris-glycine acrylamide gels. Gels were transferred to nitrocellulose membrane for two hours at 400 milliamps and then blocked for 15 to 40 minutes in five percent low fat dry milk in PBS-T (PBS with 0.1% Tween-20). Primary anti-mouse/hsod1 or anti-hsod1 antibody was added one to 5000 in milk from PBS-T for one to 16 hours followed by a three times rinse in PBS-T alone and secondary goat anti-rabbit HRP at one to 2500 in milk from PBS-T for one hour. Blots were rinsed again and visualized with ECL chemiluminescence on a Fujifilm LAS-3000 (General Electric Company).

Example 4

Determination of Expressed Hsod1 Variant Enzymatic Activities

Due to the unstable nature of superoxide anion radical, an indirect assay must be used to assess enzymatic activity. Total cell lysate was prepared from 10× pellet volume sonicated 0.1% NP-40 in TN and equivalent polypeptide amounts as measured by assay were run on 8% or 4 to 20% tris-glycine acrylamide gels in TG with 20% methanol at four degrees Celsius and 100 constant volts for four to six hours, without denaturant or reductant added. The gel was retrieved and soaked in 50 mM potassium bicarbonate buffer containing 65 μg/mL riboflavin and 280 μg/mL nitro blue tetrazolium, pH 7.6. After incubating two to 40 minutes, the solution was aspirated and 0.1% TEMED in 50 mM potassium bicarbonate buffer was added to the gel. The gel was immediately exposed to white light from a bright box and imaged on an Agfa Duoscan, with contrast increased. Densitometry was employed to measure band intensities relative to wild-type. This method was compared and validated with data of identical mutants from pulse radiolysis experiments.

What is claimed is:

1. A mutant "human superoxide dismutase 1" (hsod1) variant, wherein the wild-type (unmutated) hsod1 has a polypeptide sequence that is at least 80% identical to SEQ ID NO:1, said hsod1 having one or more mutations selected from the group consisting of:
   a) a substitution of the 21st Glu residue for Gln or Asn;
   b) a substitution of the 24th Glu residue for Gln or Asn;
   c) a substitution of the 40th Glu residue for Gln or Asn;
   d) a substitution of the 77th Glu residue for Gln or Asn;
   e) a substitution of the 78th Glu residue for Gln or Asn;
   f) a substitution of the 100th Glu residue for Gln or Asn;
   g) a substitution of the 121st Glu residue for Gln or Asn;
   h) a substitution of the 132nd Glu residue for Asn; and
   i) a substitution of the 133rd Glu residue for Asn.

2. A composition comprising the polypeptide of claim 1.

3. An isolated nucleic acid encoding the polypeptide of claim 1.

4. A recombinant nucleic acid comprising the isolated nucleic acid of claim 3.

5. An isolated host cell comprising the recombinant nucleic acid of claim 4.

* * * * *